US009072293B2

(12) United States Patent
Yoo et al.

(10) Patent No.: US 9,072,293 B2
(45) Date of Patent: Jul. 7, 2015

(54) CYCLOPROPENES AND METHOD FOR APPLYING CYCLOPROPENES TO AGRICULTURAL PRODUCTS OR CROPS

(75) Inventors: Sang-Ku Yoo, Gyeonggi-do (KR); Jin Wook Chung, Seoul (KR)

(73) Assignee: Erum Biotechnologies Inc., Gyeonggi-Do (KR)

( * ) Notice: Subject to any disclaimer, the term of this patent is extended or adjusted under 35 U.S.C. 154(b) by 0 days.

(21) Appl. No.: 13/581,797

(22) PCT Filed: Apr. 15, 2011

(86) PCT No.: PCT/KR2011/002692
§ 371 (c)(1),
(2), (4) Date: Aug. 29, 2012

(87) PCT Pub. No.: WO2011/132888
PCT Pub. Date: Oct. 27, 2011

(65) Prior Publication Data
US 2012/0322662 A1  Dec. 20, 2012

(30) Foreign Application Priority Data

Apr. 22, 2010  (KR) .................. 10-2010-0037348

(51) Int. Cl.
| A01N 31/08 | (2006.01) |
| A01N 27/00 | (2006.01) |
| C07C 15/12 | (2006.01) |
| A01P 21/00 | (2006.01) |
| A01N 31/14 | (2006.01) |
| A01N 55/00 | (2006.01) |
| C07F 7/08 | (2006.01) |
| C07C 13/28 | (2006.01) |
| C07C 43/215 | (2006.01) |

(52) U.S. Cl.
CPC .............. *A01N 27/00* (2013.01); *A01N 31/14* (2013.01); *A01N 55/00* (2013.01); *C07F 7/0818* (2013.01); *C07C 13/28* (2013.01); *C07C 2101/02* (2013.01); *C07C 43/215* (2013.01)

(58) Field of Classification Search
CPC ....... A01N 27/00; A01N 31/14; A01N 55/00; C07C 13/28; C07C 2101/02; C07C 43/215; C07F 7/0818
USPC ................ 504/354, 357; 568/331; 585/25
See application file for complete search history.

(56) References Cited

U.S. PATENT DOCUMENTS

| 5,518,988 A | 5/1996 | Sisler et al. |
| 6,017,849 A | 1/2000 | Daly et al. |
| 6,194,350 B1 | 2/2001 | Sisler |
| 6,426,319 B1 | 7/2002 | Kostansek |
| 6,444,619 B1 | 9/2002 | Kostansek |
| 6,452,060 B2 | 9/2002 | Jacobson |
| 6,548,448 B2 | 4/2003 | Kostansek |
| 6,762,153 B2 | 7/2004 | Kostansek et al. |
| 6,953,540 B2 | 10/2005 | Chong et al. |
| 2001/0019995 A1 | 9/2001 | Sisler |
| 2004/0077502 A1* | 4/2004 | Jacobson et al. ............. 504/313 |
| 2004/0192554 A1 | 9/2004 | Kashimura et al. |
| 2005/0065033 A1* | 3/2005 | Jacobson et al. ............. 504/343 |
| 2008/0286426 A1* | 11/2008 | Yoo .............................. 426/321 |

FOREIGN PATENT DOCUMENTS

| JP | 10-94741 | 4/1998 |
| KR | 10-2003-0086982 | 11/2003 |
| KR | 1020030086982 A | * 11/2003 |
| KR | 10-2007-0053113 | 5/2007 |
| KR | 1020070053113 | 5/2007 |
| KR | 1020070053113 A | * 5/2007 |
| WO | WO 02/068367 | 9/2002 |

OTHER PUBLICATIONS

IPRP for related PCT/KR2011/002692 issued on Oct. 23, 2012 and its English translation.
ISR for related PCT/KR2011/002692 mailed on Jan. 2, 2012 and its English translation.
Fumie Sato, et al. "Generation of a Silylethylene-Titanium Alkoxide Complex. A Versatile Reagent for Silylethylation and Silylethylidenation of Unsaturated Compounds". *J. Org. Chem.* 65(2000), 6217-6222.
W. E. Billups and Micahel M. Haley, "Spiropentadiene" *J. Am. Chem. Soc.* 113(1991), 5084-5085.
Sisler, et al. "The effect of dialkylamine compounds and related derivatives of 1-methylcyclopropene in counteracting ethylene responses in banana fruit". *Postharvest Biology and Technology* 51(2009), 43-48.
Office action dated Jul. 1, 2013 from corresponding New Zealand Patent Application No. 602296 (3 pages).
Fisher and Applequist. "Synthesis of 1-Methylcyclopropene." J. Org. Chem. 30 (1965) 2089-2090.
Magid, et al. "An Efficient and Convenient Synthesis of I-Methylcyclopropene." J. Org. Chem. 36 (1971) 1320-1321.
Arquiza, J.M.R., et al. "1-Methylcyclopropene Interactions with Diphenylamine on Diphenylamine Degradation, α-Farnesene and Conjugated Trienol Concentrations, and Polyphenol Oxidase and Peroxidase Activities in Apple Fruit." J. Agric. Food Chem. 53 (2005), 7565-7570.
Martinez-Romero, et al. "1-Methylcyclopropene Increases Storability and Shelf Life in Climacteric and Nonclimacteric Plums." J. Agric. Food Chem. 51 (2003), 4680-4686.
Argenta, et al. "Influence of 1-methylcyclopropene on Ripening, Storage Life, and Volatile Production by d'Anjou cv. Pear Fruit." J. Agric. Food Chem. 51 (2003), 3858-3864.

(Continued)

Primary Examiner — Janet Epps-Smith
Assistant Examiner — Courtney Brown
(74) Attorney, Agent, or Firm — Ladas & Parry, LLP

(57) ABSTRACT

Disclosed is a method for directly preparing in situ cyclopropenes for inhibiting ethylene action facilitating ripening and aging of plants via reaction of a cyclopropene precursor such as a compound of Formula (2) or Formula (3) with a fluoride ($F^-$) and immediately applying the same to plants, and an aryl group-containing 1-alkylcyclopropene of Formula (6) effective for inhibiting the action of ethylene.

17 Claims, No Drawings

(56) References Cited

OTHER PUBLICATIONS

Botondi, et al. "Influence of Ethylene Inhibition by 1-Methylcyclopropene on Apricot Quality, Volatile Production, and Glycosidase Activity of Low- and High-Aroma Varieties of Apricots." J. Agric. Food Chem. 51 (2003), 1189-1200.

Fan and Mattheis. "Impact of 1-Methylcyclopropene and Methyl Jasmonate on Apple Volatile Production." J. Agric. Food Chem. 47 (1999), 2847-2853.

Baird, M.S., et al. "The Preparation and Lithiation of 1-Halogenocyclopropenes." J. Chem. Soc. Perkin Trans. 1, 1986, 1845-1854.

Baird, M.S., et al. "(R)-1, 3-Dimethylcyclopropene-One Isomer of the Smallest Chiral Hydrocarbon." J. Chem. Soc. Perkin Trans 1, 1993, 321-326.

Binger, Paul. "Eine einfache Syntehse von 3,3-Dimethylcyclopropen." Synthesis, 1974, p. 190 (translated by ABBYY PDF Transformer 3.0 and Google Translate).

Billups and Haley. "Spiropentadiene" J. Am. Chem. Soc., 113 (1991); 5084-5085.

Billups, et al. "1,3-Bridged Cyclopropenes." J. Am. Chem. Soc., 113 (1991), 7980-7984.

Haley, et al. "Synthesis of Alkenyl-and Alkynylcyclopropenes." Tetrahedron Lett. 36 (1995), 3457-3460.

Chan, T.H. and Massuda, D. "Entry into the cyclopropene system via vinylsilanes." Tetrahedron Lett. 16 (1975) 3383-3386.

Mizojiri, et al. "Generation of a Silylethylene-Titanium Alkoxide Complex. A Versatile Reagent for Silylethylation and Silylethylidenation of Unsaturated Compounds." J. Org. Chem. 65 (2000), 6217-6222.

Banwell, M.G., et al. "Generation and Solution-phase Behaviour of Some 2-Halogeno-1, 3-ring-fused Cyclopropenes." J. Chem. Soc. Perkin Trans 1, 1993, 945.

Billups, et al. "Synthesis of Oxaspiropentene." Org. Lett., 1 (1999), 115-116.

N.I. Yakushkina and I.G. Bolesov. "Dehydrohalogenation of Monohalogenocyclopropanes as a Method for the Synthesis of Sterically Screened Cyclopropenes." The Russian Journal of Organic Chemistry. vol. 15 (1979). pp. 853-859.

Office Action from corresponding Australian Patent Application No. 2011243466 dated Jun. 6, 2014.

Office Action from corresponding Chinese Patent Application No. 201180016516.X dated Apr. 2, 2014 with summary in English.

Office Action from corresponding Chinese Patent Application No. 201180016516.X dated Jan. 2, 2014 with summary in English.

Office Action from corresponding Chinese Patent Application No. 201180016516.X dated Jun. 27, 2014 with summary in English.

Office Action from corresponding Chinese Patent Application No. 201180016516.X dated Sep. 9, 2013 with summary in English.

Office Action from corresponding European Patent Application No. 11772176.1 dated Sep. 8, 2014.

Office Action from corresponding New Zealand Patent Application No. 602296 dated Sep. 23,2013.

Office Action from corresponding Chinese Patent Application No. 201180016516.X dated Nov. 3, 2014 with English translation, or summary.

\* cited by examiner

CYCLOPROPENES AND METHOD FOR APPLYING CYCLOPROPENES TO AGRICULTURAL PRODUCTS OR CROPS

CROSS-REFERENCE TO RELATED APPLICATIONS

This application is the U.S. National Stage of International Patent Application No. PCT/KR2011/002692 filed on Apr. 15, 2011 which claims priority to Korean Application No. 10-2010-0037348 filed Apr. 22, 2010, the disclosures of which are hereby incorporated by reference in their entireties.

TECHNICAL FIELD

The present invention relates to a method for preparing cyclopropenes in agricultural sites and immediately applying the same to plants. More specifically, the present invention relates to a method for inhibiting the ethylene action associated with a ripening or aging process in plants by preparing chemically unstable 1-alkylcyclopropenes via a reaction of a 1-alkylcycloproene precursor with fluoride (F⁻) and immediately applying the same to plants and a substance effective for inhibiting the ethylene action in plants.

BACKGROUND ART

Ethylene ($C_2H_4$) acts as a plant hormone which accelerates the ripening process in plants. In this regard, it is well known in the art that cyclopropenes effectively inhibit the ethylene action in plants [U.S. Pat. Nos. 5,518,988 and 6,194,350]. Of these cyclopropenes, 1-alkylcyclopropenes, represented by Formula 1 below, are very potent. In particular, 1-methylcyclopropene, a gas even at ambient temperature (b.p. ~10° C./1 atm), advantageously, can be easily applied to agricultural products in a closed warehouse without any additional spray device or system. For this reason, 1-methylcyclopropene has been widely used to keep fruits, flowers and vegetables such as apples, pears, persimmons, plums, kiwis, tomatoes, lilies and carnations, fresh.

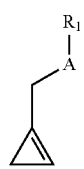

(1)

wherein A represents a straight-chain linkage having the formula of $(CH_2)_mY(CH_2)_n$ in which m and n each independently represent an integer of 0 to 3, and Y each independently represents $CH_2$, O, S or the like.

$R_1$ represents saturated or unsaturated $C_3$-$C_{20}$ alkyl or $C_4$-$C_{10}$ aryl, furanyl, pyranyl or thiofuranyl, wherein alkyl or aryl may be substituted with fluoride, chloride, bromide, iodide, oxygen, sulfur, nitrogen, silicon, phosphorus or the like.

Generally, cyclopropenes such as cyclopropene, 1-methylcyclopropene, 1,2-dimethylcyclopropene, 1,3-dimethylcyclopropene, 1-ethylcyclopropene, 1-hexylcyclopropene and 1-octylcyclopropene are readily decomposed and their half life are thus only 0.5~20 hours at room temperature. For this reason, it is impractical to synthesize, store and apply these compounds using a routine method known to the agrochemical industry. The decomposing process of these cyclopropenes is a dimerization reaction in which two molecules of cyclopropenes combine each other.

Accordingly, these cyclopropenes are much more stable in a dilute state. For example, 1-methylcyclopropene (b.p. ~10° C./1 atm) is so unstable that it may explode at room temperature when it is purified at a high concentration. However, the half life for 1,000 ppm (v/v) or less concentration of 1-methylcyclopropene is 10 days or longer at room temperature. Furthermore, 1-methylcyclopropene can be stably stored for one year or more, when the individual molecules can be thoroughly separated using α-cyclodextrin. This method has been actually utilized in an area to store agricultural products for a long time [U.S. Pat. Nos. 6,017,849, 6,426,319, 6,444,619, 6,548,448, 6,762,153 and 6,953,540].

Meanwhile, rather than the method for storing 1-methylcyclopropene with low stability, a method for preparing 1-methylcyclopropene in situ and for immediately using the same has been also utilized in the area to store agricultural products and crops. For example, the inventor of the present invention (Korean Patent Application No. 2006-0112039) has suggested a method and an apparatus for directly preparing 1-methylcyclopropene in situ and treating plants with the same. This application discloses the preparation of 1-methylcyclopropene via the reaction of β-halocyclopropylsilane or its chemical equivalents thereof with a fluoride (F⁻). This method relates to a method for preparing a highly volatile compound such as 1-methylcyclopropene in situ and immediately treating agricultural products with the same which is considerably effective when agricultural products are treated primarily in an independent warehouse or an additional closed treatment area.

However, because these methods are limited to only utilizing highly volatile substances such as 1-methylcyclopropene in closed areas, they are disadvantageously not suitable for applying a variety of 1-alkylcyclopropenes to agricultural products in open areas such as rice paddies, fields, meadows, orchards, forests and large greenhouses rather than closed areas.

Conventional agrochemical agents are applied to plants via a series of processes (that is, processes such as synthesis, formulation or spraying of agrochemical agents) including (i) the synthesis of an active ingredient, (ii) the formulation of the same using a surfactant, a stabilizing agent or the like and (iii) the spray of the same to agricultural produces in rice paddies, fields, orchards, farms, forests or the like. These processes commonly require from one or two months at minimum to a year or longer at maximum.

However, as mentioned above, 1-alkylcyclopropenes are readily decomposed due to low chemical stability thereof and desired effects cannot be obtained via a typical process for preparing and treating general agrochemical agents such as pesticides. Consequently, 'a method for storing 1-alkylcyclopropenes at an ultra-cold condition (−50° C. or below)' or 'a method for storing 1-alkylcyclopropenes by encapsulating the same to a substance such as cyclodextrin' is inevitable to apply 1-alkylcyclopropenes to agricultural produces or plants in fields.

DISCLOSURE

Technical Problem

Therefore, the present invention has been made to solve the above and other technical problems that have yet to be resolved.

Accordingly, it is an object of the present invention to provide a method for freely applying 1-alkylcyclopropenes to agricultural produces in open fields such as rice paddies, fields, forests, orchards, greenhouses, etc.

Technical Solution

Accordingly, to achieve the object and other advantages of the invention, provided is a method for treating plants with 1-alkylcyclopropene represented by Formula 1 below in closed areas as well as open areas, the method comprising:

(a) mixing (i) a 1-alkylcyclopropene precursor-containing agent of Formula 2 or 3 and (ii) a fluoride containing agent, separately supplied to prepare 1-alkylcyclopropene of Formula 1;

(b) simultaneously or continuously with step (a), phase-separating 1-alkylcyclopropene of Formula 1 from the reaction solution; and (c) applying the 1-alkylcyclopropene of Formula 1 to plants, wherein the steps are carried out in situ.

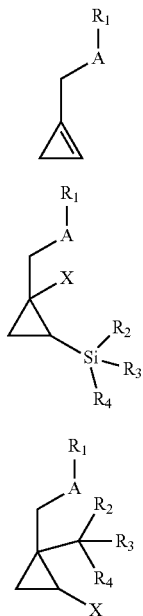

wherein A represents a straight-chain linkage having the formula of $(CH_2)_m Y(CH_2)_n$, in which m and n each independently represent an integer of 0 to 3 and Y each independently represents $CH_2$, O or S;

$R_1$ represents saturated or unsaturated $C_3$-$C_{20}$ alkyl or $C_4$-$C_{10}$ aryl, furanyl, pyranyl, or thiofuranyl, each of which may be substituted with at least one selected from the group consisting fluoride, chloride, bromide, iodide, oxygen, sulfur, nitrogen and silicon; $R_2$, $R_3$ and $R_4$ each independently represent saturated or unsaturated $C_1$-$C_{10}$ alkyl or alkoxy, $C_6$-$C_{10}$ aryl or aryloxy, $C_1$-$C_{10}$ primary amine or secondary amine, or halogen; and X represents halogen or $OSO_2T$, in which T represents hydrogen, saturated or unsaturated $C_1$-$C_{10}$ alkyl, alkoxy or aryl, aryloxy, amine, halogen or hydroxy.

In accordance with the method of the present invention, 1-alkylcyclopropenes of Formula 1 are directly prepared in situ and are applied to crops or plants via a series of processes, thereby enabling application of the alkylcyclopropenes to crops or plants at a predetermined concentration, before chemically unstable 1-alkylcyclopropenes are removed due to the polymerization reaction.

In the present invention, there are a variety of methods for applying 1-alkylcyclopropenes to crops or plants. The methods include, but are not limited to, direct application of the substance and application in the form of water dispersible powders or granules.

Alkyl used herein includes alkyl substituted with hydroxyl, halogen, alkoxy, cycloalkyl, aryl, amine, thioalkoxy or the like. In addition, aryl used herein includes aryl substituted with lower alkyl, alkoxy, thioalkoxy, nitro, halogen, amine or the like.

The compound of Formula 2 may be synthesized in accordance with a series of processes depicted in the following Reaction Scheme 1, based on the method reported by Fumie Sato, et al. (*J. Org. Chem.* 65 (2000), 6217~6222).

<Reaction Scheme 1>

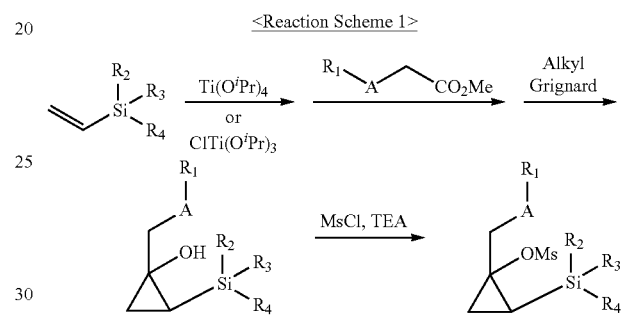

wherein A, $R_1$, $R_2$, $R_3$ and $R_4$ are defined in Formula 2 above.

Specifically, alkyl Grignard reagents such as ethyl, propyl, butyl or isopropyl; titanium (IV) isopropxide or chlorotitanium (IV) triisopropoxide; trialkylvinylsilane; and alkanoic acid ester are reacted with one another to obtain a mixture of trans and cis 1-hydroxyl-1-methylcyclopropane (2:1 to 5:1) and the compound is reacted with methanesulfonylchloride to obtain the compound of Formula 2 as a mixture.

The substance of Formula 3 may be synthesized in accordance with a series of processes depicted in the following Reaction Scheme 1, based on the method reported by W. E. Billups, et al. *J. Am. Chem. Soc.* 113 (1991), 5084~5085.

<Reaction Scheme 2>

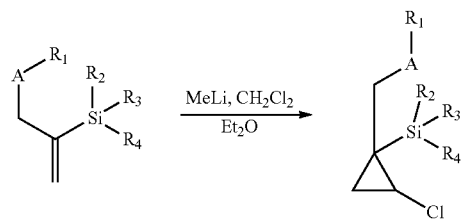

wherein A, $R_1$, $R_2$, $R_3$ and $R_4$ are defined in Formula 3 above.

Specifically, 1-alkylvinyltrialkylvinylsilane reacts with carbene obtained via reaction of methyllithium with dichloromethane to obtain a compound of Formula 3.

In Formulae 1 to 3, $R_1$ represents saturated or unsaturated $C_3$-$C_{20}$ alkyl or $C_4$-$C_{10}$ aryl, furanyl, pyranyl or thiofuranyl, each of which may be substituted with at least one selected from the group consisting of fluoride, chloride, bromide, iodide, oxygen, sulfur, nitrogen, silicon and phosphorous.

The 1-alkylcyclopropenes of Formula 1 can be prepared by simply mixing cyclopropene precursors of Formulae 2 and 3 with organic salts or metal salts containing fluoride (NaF, LiF, KF, CsF and $MgF_2$). Specific examples of such fluoride salts include, but are not limited to $Bu_4NF$, $Pr_4NF$, $Me_4NF$ $Et_4NF$, n-$Pentyl_4NF$, n-$Hexyl_4NF$, $BnBu_3NF$, $BnPr_3NF$, $BnMe_3NF$ and $BnEt_3NF$. Preferred is tetraalkylammonium fluoride of Formula 4, and particularly preferred are alkylammonium salts having carbon atoms of 10 or more such as $Bu_4NF$, n-$Pentyl_4NF$, n-$Hexyl_4NF$ and $BnEt_3NF$.

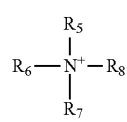

(4)

wherein $R_5$, $R_6$, $R_7$ and $R_8$ each independently represent $C_1$-$C_{20}$ alkyl or $C_6$-$C_{15}$ aryl.

Preferably, a solvent is used to efficiently mix the agent (i) and/or the agent (ii) in step (a). Specifically, examples of solvents include, but are not limited to, DMSO, DMF, THF, dimethylsulfone, dimethylacetamide, 2-pyrrolidinone, 1-methyl-2-pyrrolidinone, 1,4-dioxane, diethyl ether, tert-butyl methyl ether, 1-methyl-2-pyrrolidinone, diglyme, ethyl acetate, acetonitrile, ethanol, isopropanol, butanol, propanol, ethylene glycol, toluene, xylene, water and mixtures thereof. Preferably, the agent (i) and/or the agent (ii) are dissolved in a polar aprotic solvent among these solvents. Particularly preferably, the polar aprotic solvent is at least one selected from the group consisting of non-volatile solvents such as DMSO, DMF, dimethylsulfone, dimethylacetamide, 2-pyrrolidinone and 1-methyl-2-pyrrolidinone.

In a preferred embodiment, phase separation in step (b) is carried out by mixing a polar solvent and a non-polar solvent with a reaction solvent. The polar solvent is at least one selected from the group consisting of water, acetonitrile and ethylene glycol. The non-polar solvent is at least one selected from xylene, benzene, toluene, methylsilene, and ethylbenzene, propylbenzene, cumene, a mixed solvent of aromatic compounds (Kokosol), pentane, hexane, heptane, octane, a mixed solvent of saturated hydrocarbon compounds (petroleum ether), ethyl ether, butylether, and methyl tertiary butyl ether (MTBE).

In step (c), 1-alkylcyclopropene is preferably dissolved in a non-polar solvent prior to application.

In a preferred embodiment, step (c) may further comprise mixing the phase-separated 1-alkylcyclopropene with a liquid solvent, a surfactant and a stabilizing agent. Preferably, the liquid solvent is at least one selected from the group consisting of water, alcohol, pentane, hexane, petroleum ether, ethyl ether and MTBE. Although the surfactant may be selected from both cationic surfactants and anionic surfactants, anionic surfactants are more economical and convenient. The stabilizing agent is at least one selected from the group consisting of water-soluble polymers such as polyacrylic acid, polymethacrylic acid, hydroxypropylmethyl cellulose (HPMC) and neutral surfactants such as polyethylene glycol isooctylphenyl ether, polyethylene glycol isooctylcyclohexyl ether and polyethylene glycol tristyrenylphenyl ether.

In the preparation step, the contents of 1-alkylcyclopropene, the solvent, the surfactant and the stabilizing agent are not particularly limited, but may fall within the following given range as a non-limiting example.

The 1-alkylcyclopropene phase-separated in phase-separation step (b) may be present in an amount of 1 to 30% by weight, based on the total weight of the solution in the phase-separation step. In step (c), the liquid solvent may be present in an amount of 50 to 99% by weight, preferably 60 to 95% by weight, based on the total weight of the mixed solution. In step (c), the surfactant may be present in an amount of 1 to 40% by weight, preferably 5 to 30% by weight, based on the total weight of the mixed solution. In step (c), the stabilizing agent may be present in an amount of 0.01 to 20% by weight, preferably 0.1 to 10% by weight, based on the total weight of the mixed solution.

In another preferred embodiment, step (c) may further comprise diluting 1-alkylcyclopropene with a liquid solvent and/or a solid extender, followed by dispersion. Preferably, the liquid solvent useful as the extender is at least one selected from the group consisting of water, ethylene glycol, alcohol, pentane, hexane, petroleum ether, toluene, xylene, Kokosol, MTBE and ethyl ether, and the solid extender is at least one selected from the group consisting of starch, quicklime and clay.

The concentration of liquid solvent may be varied depending on the subject to be treated. The liquid solvent is preferably diluted 10 to 100,000 times upon use, based on the total weight of the mixed solution phase-separated in step (b). In addition, the solid extender is more preferably diluted 100 to 10,000 times, based on the total weight of the mixed solution phase-separated in step (b) upon use.

The overall process described above is depicted by the following Reaction Scheme 3.

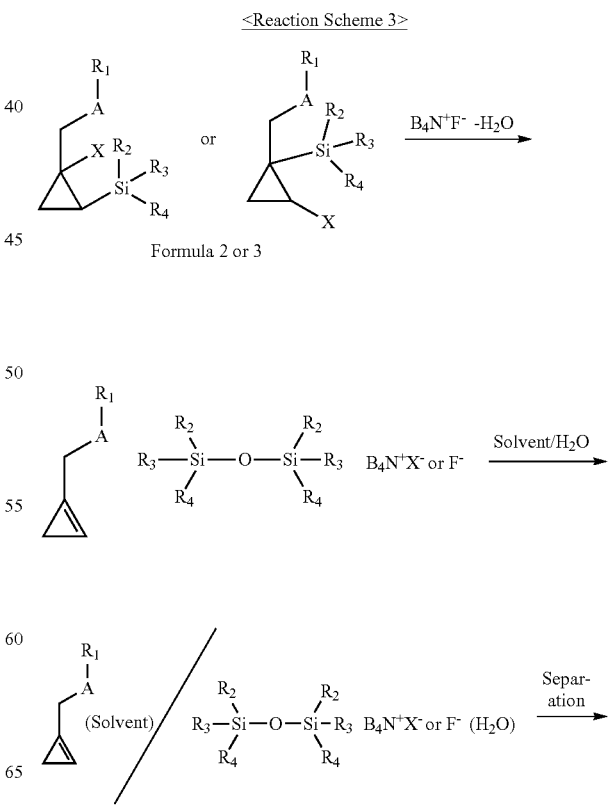

-continued

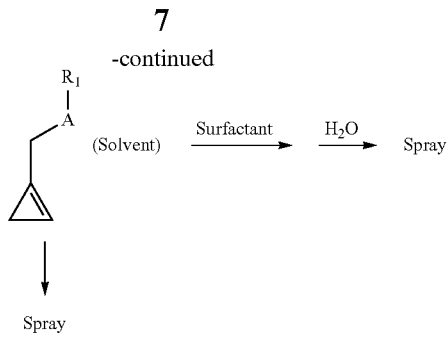

Spray

Preferably, the process from the preparation of 1-alkylcyclopropenes and its application to plants is commonly completed within 50 hours. In particular, when the process from the preparation of 1-alkylcyclopropenes and its application to plants exceeds 50 hours, an appropriate concentration of 1-alkylcyclopropene cannot be applied to crops or plants due to short half-life of 1-alkylcyclopropene. More preferably, the application process is completed within 20 hours. As the application period shortens, the expected efficacy increases.

Further, the present invention provides a method for treating plants with alkylcyclopropene of Formula 1 in an open area, comprising:

(a) mixing (i) a 1-alkylcyclopropene precursor-containing agent of Formula 2 or 3 and (ii) a fluoride salt-containing agent, separately supplied to prepare 1-alkylcyclopropene of Formula 1;

(b) separating and extracting 1-alkylcyclopropene of Formula 1 from the reaction solution;

(c) mixing the 1-alkylcyclopropene with a liquid solvent, a surfactant and a stabilizing agent;

(d) optionally, diluting the 1-alkylcyclopropene with a liquid solvent and/or a solid extender, followed by dispersion; and (e) applying the extracted solution, mixed solution or diluted solution obtained in step (b), (c) or (d) to plants,
wherein the steps are carried out in situ.

Further, the present invention provides a kit for preparing 1-alkylcyclopropene in situ to treat plants with alkylcyclopropene of Formula 1 in an open area, comprising:

(i) the 1-alkylcyclopropene precursor-containing agent of Formula 2 or Formula 3; (ii) the fluoride salt-containing agent; and (iii) a liquid solvent containing a polar solvent and a non-polar solvent.

The kit separately provides the 1-alkylcyclopropenes precursor and the fluoride salt and additionally provides the polar solvent and the non-polar solvent. Accordingly, the kit enables direct application of 1-alkylcyclopropene to plants in fields by preparing 1-alkylcyclopropene according to the method of the present invention immediately prior to application to plants or crops and separating the 1-alkylcyclopropene via phase-separation.

Further, the present invention provides a compound of Formula 6 which is easily formulated, exhibits superior chemical stability, is readily analyzed and exhibits excellent performance, when formulated in situ and applied to plants by the method mentioned above.

Cyclopropene derivatives developed to date for the purpose of controlling ethylene action of plants are derivatives defined by the following Formula 5 such as 1-methylcyclopropene, 1-ethylcyclopropene, 1-propylcyclopropene, 1-butylcyclopropene, 1-pentylcyclopropene, 1-hexylcyclopropene, 1-octylcyclopropene and 1-decylcyclopropene, and it is known that 1-alkylcyclopropene derivatives substituted with $C_1$-$C_{15}$ straight chain alkyl groups exhibit superior efficacy [U.S. Pat. No. 6,194,350], while amine-containing alkylcyclopropene derivatives exhibit considerably low efficacy [Postharvest Biology and Technology 51 (2009), 4348]. However, analysis methods for detecting these 1-alkylcyclopropenes are extremely limited, since these 1-alkylcyclopropene derivatives simply substituted with straight alkyl groups have no chromophore, emitting or absorbing light. That is, a gaseous substance at room temperature, such as cyclopropene or 1-methylcyclopropene, can be analyzed by gas chromatography even at a low temperature of 50° C. or less. However, 1-alkylcyclopropenes having carbon atoms of 10 or more in total should be generally exposed to an oven at a high temperature for the analysis by gas chromatography. However, cyclopropenes easily decompose under high temperature conditions and are unpractical for the analysis. Furthermore, because these 1-alkylcyclopropenes have no chromophore for UV or visible absorption and are highly non-polar substances composed of hydrocarbon alone, even a general HPLC analysis is thus formidable.

wherein $R_9$ represents straight $C_1$-$C_{15}$ alkyl.

For this reason, a novel derivative of Formula 6 containing an aryl group with a chromophore sensitive to UV was designed and showed superior results that it can be readily detected and analyzed, as compared to derivatives containing no aryl group.

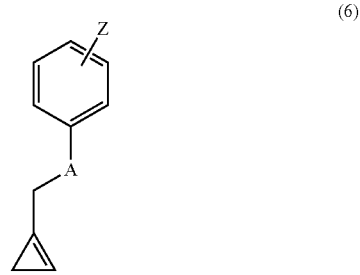

wherein A represents a straight-chain linkage having the formula of $(CH_2)_mY(CH_2)_n$ in which m and n each independently represent an integer of 0 to 3 and Y each independently represents $CH_2$, O or S; and Z represents at least one selected from the group consisting of hydrogen, alkyl, alkoxy, halogen, nitro and nitrile.

The characteristics of the compound of Formula 6 will be described below.

First, a variety of analysis is available from the synthetic process of raw materials and the chemical stability of the compound increases.

A variety of analysis methods can be used to analyze the derivatives of Formula 6, since the absorbance of cyclopropenes containing an aryl group can be easily measured in the UV range. It can be confirmed that the chemical stability of the derivatives increases, when the length of chains to link an aryl ring to a cyclopropene ring is 2 or more. That is, as shown in Table 1 below, while cyclopropenes having aryl substituents are considerably unstable, provided that the chain to link the cyclopropene ring to the aryl ring has a length of 0 {1-phenylcyclopropene} or 1 {1-benzylcyclopropene}, cyclopropenes are considerably stable, provided that the chain has a length of 2 {A=CH$_2$: 1-(2-phenylethyl)cyclopropene}, and cyclopropenes are much more stable, provided that the chain has a length of 3 {A=CH$_2$CH$_2$: 1-(3-phenylpropyl)cyclopropene}, 4 {A=CH$_2$CH$_2$CH$_2$: 1-(4-phenylbutyl)cyclopropene} or 5 {A=CH$_2$CH$_2$CH$_2$CH$_2$:1-(5-phenylpentyl)cyclopropene}. It is supposed that the stability of cyclopropenes increase due to the fact that π electrons of aryl groups affect π electrons of cyclopropenes.

The following Table 1 summarizes the relative chemical stability of cyclopropenes having a chain length of 2, 3, 4 or 5, based on the chemical stability of cyclopropenes having a chain length of 1. In the case of cyclopropene having a chain length of 1, the structure thereof can be confirmed via $^1$H-NMR within one hour following synthesis (degraded to a level of 50% or more within one hour at 30° C.). In the case of cyclopropene having a chain length of zero, synthesis thereof was attempted in accordance with the present invention, but was impossible by a conventional method. Meanwhile, in the case of cyclopropenes having a chain length of 2 or more, the structure thereof can be precisely confirmed by $^1$H-NMR as well as $^{13}$C-NMR. The stability of these cyclopropenes was measured by $^1$H-NMR while NMR cells (CDCl$_3$) were stored at −20° C. or room temperature. In particular, cyclopropenes having chains of 3 or more were so stable that their half-life reached 5 days or longer at −20° C. or lower. In $^1$H-NMR analysis, the stability was evaluated by comparing integral values at 4 to 6.5 ppm (1H) and 0.8 to 0.9 ppm (2H), characteristic peaks of 1-alkylcyclopropenes, using a small amount of 1,1,3,3-tetramethylurea (2.80 ppm) as an internal standard. Furthermore, the stability was also qualitatively evaluated by comparing integral value of the peak newly generated adjacent to the peak of the olefin proton of cyclopropene ring, as a 1-alkylcyclopropene compound is decomposed.

TABLE 1

| A | — | CH$_2$ | CH$_2$CH$_2$ | CH$_2$CH$_2$CH$_2$ | CH$_2$CH$_2$CH$_2$CH$_2$ |
|---|---|---|---|---|---|
| Z | H | H | H | H | H |
| Chain Length | 1 | 2 | 3 | 4 | 5 |
| Stability | 1 | >10 | >>10 | >>10 | >>10 |
| A | — | CH$_2$ | CH$_2$CH$_2$ | CH$_2$CH$_2$O | CH$_2$CH$_2$CH$_2$O |
| Z | 4-OCH | 4-OCH$_3$ | 4-OCH$_3$ | H | H |
| Chain Length | 1 | 2 | 3 | 4 | 5 |
| Stability | ~1 | >10 | >>10 | >>10 | >>10 |

Second, derivatives containing an aryl group exhibit superior inhibitory activity on the ethylene action in plants.

It was confirmed that these 1-alkylcyclopropenes containing an aryl group (Formula 6) are chemically stable and efficiently inhibit the ethylene action in plants, when applied to plants in a liquid formulation such as emulsion or oil. This can be confirmed by comparing relative reddening rate in tomatoes in the following Experimental Examples 1, 2 and 3. At this time, as the reddening rate decreases, the inhibitory activity on the ethylene action in plants improves. That is, in efficacy comparison test for cyclopropenes containing an aryl group and 1-hexylcyclopropene, cyclopropenes having a chain length of 2 or longer, in particular, of 3 or longer exhibit superior effects. That is, 1-alkylcyclopropenes containing an aryl group (Formula 6) exhibit considerably superior efficacy of delaying reddening rate on tomato, as compared to straight alkyl substituted cyclopropenes containing no aryl group (Formula 5).

Third, 1-alkylcyclopropenes containing an aryl group (Formula 6) have an additional advantage of considerably easy formulation, as compared to straight alkyl substituted cyclopropenes containing no aryl group (Formula 5).

That is, in steps (a), (b) and (c) for preparing and formulating 1-alkylcyclopropenes involved in the method according to the present invention, simple 1-alkylcyclopropenes (Formula 5) are still highly volatile and are thus readily evaporated, and do not easily form a complete formulation with a mixed agent of a liquid solvent such as toluene, Kokosol and xylene, and an anionic surfactant, commonly used in the formulation process, but are present in a colloidal phase. On the other hand, 1-alkylcyclopropenes containing an aryl group in accordance with the present invention (Formula 6) are highly non-volatile per se and are thus stably present in a solution, and form a clear and transparent solution with a mixed agent of a liquid solvent such as toluene or Kokosol, and an anionic surfactant, obtaining a complete formulation.

Consequently, it can be seen that the case where the formulated derivatives of Formula 6 were applied in an emulsion diluted with water to plants (see Table 2 shown in Example 1), and the case where the derivatives were applied in an oil-based formation to plants without any treatment (see Table 3 shown in Example 2) exhibited more potent efficacy, as compared to 1-hexylcyclopropene of Formula 5.

For this reason, the present invention provides 1-alkylcyclopropenes of Formula 6 which are formulated in situ by the method mentioned above and are suitable for application to plants.

Advantageous Effects

As apparent from the foregoing, the present invention provides easy and simple preparation of 1-alkylcyclopropenes well known as inhibitors of the ethylene action in plants such as fruits, flowers and vegetables in closed agricultural areas as well as opened agricultural areas and immediate application thereof to plants. As a result, it is expected that 1-alkylcyclopropenes can efficiently control a variety of physiological actions of plants associated with ethylene in both cases of post-harvest as well as pre-harvest.

BEST MODE

Now, the present invention will be described in more detail with reference to the following Examples. The Preparation Examples are representatively provided only to illustrate the synthesis process of Formula 2 or Formula 3 and should not be construed as limiting the scope and spirit of the present invention.

Preparation Example 1

Synthesis of (trans)-1-benzyl-1-(methansulfonyloxy)-2-(trimethylsilyl)cyclopropane 2.02 g of magnesium and 30 ml of ethyl ether were placed in a 100 ml three-neck round bottom flask and 6.3 g of 2-chloropropane was slowly added thereto, to prepare a Grignard solution. Meanwhile, 10.7 g of titanium (IV) isopropoxide and 3.7 g of vinyltrimethylsilane were placed in another 100 ml three-neck round bottom flask cooled to −78° C., and the above-prepared Grignard solution was slowly added thereto for 30 minutes. The reaction solution thus obtained was warmed to −50° C. and then vigorously stirred for 2 hours. 4.8 g of phenylacetic acid methyl ester was slowly added over 30 min, while the reaction solution was maintained at −50° C. The reaction solution was warmed to −20° C., vigorously stirred for 1 hour, warmed to 0° C., and then vigorously stirred for another one hour. Finally, the reaction solution was warmed to room temperature and 7 ml of concentrated brine was added to the solution. The resulting solution was filtered through Celite which was then thoroughly washed once more with 20 ml of ether. The filtrate thus obtained was dried over anhydrous magnesium sulfate (MgSO$_4$) and was concentrated by the evaporation of solvent at a low temperature of 30° C. or less. 1-methyl-1-hydroxy-2-(trimethylsilyl)cyclopropane was purely separated from the resulting product using silica gel.

Results of $^1$H-NMR and $^{13}$C-NMR are given below.

$^1$H-NMR (DMSO-d$_6$, δ): 7.308 (2H, m, J=1.6, 7.2 Hz), 7.259 (2H, m, J=1.6, 7.2 Hz), 7.172 (1H, m, J=1.6, 7.2 Hz), 5.209 (1H, s, b), 2.988 (1H, dd, J=1.2, 14.8 Hz), 2.539 (1H, d, J=14.8 Hz), 0.832 (1H, ddd, J=1.2, 4.0, 11.6 Hz), 0.508 (1H, dd, J=4.0, 8.4 Hz), 0.000 (9H, s), −0.022 (1H, dd, J=8.4, 11.6 Hz).

$^{13}$C-NMR (DMSO-d$_6$, δ): 140.839, 129.973, 128.464, 126.386, 59.116, 43.047, 17.332, 14.341, 0.000.

2.3 g of the alcohol compound obtained above was dissolved in 15 ml of dichloromethane and 2.5 ml of triethylamine was added thereto. The reaction solution was cooled to 0° C., 1.5 g of methansulfonyl chloride was slowly added, and vigorously stirred for one hour. 10 ml of saturated NaHCO$_3$ was added to the reaction solution to complete the reaction. An organic layer was separated from the resulting reaction, concentrated and purified to obtain (trans)-1-benzyl-1-(methanesulfonyloxy)-2-(trimethylsilyl)cyclopropane. The $^1$H-NMR and $^{13}$C-NMR for the product are given below.

$^1$H-NMR (CDCl$_3$, δ): 7.23~7.38 (5H, m), 3.707 (1H, dd, J=1.6, 15.6 Hz), 2.764 (3H, s), 2.662 (1H, d, J=15.6 Hz), 1.401 (1H, ddd, J=1.6, 4.2, 12.4 Hz), 0.922 (1H, dd, J=9.6, 12.4 Hz), 0.771 (1H, dd, J=4.2, 9.6 Hz), 0.138 (9H, s).

$^{13}$C-NMR (CDCl$_3$, δ): 137.578, 129.077, 128.356, 126.685, 70.037, 40.283, 39.663, 15.208, 12.737, −1.220.

Preparation Example 2

Synthesis of (trans)-1-(2-phenylethyl)-1-(methanesulfonyloxy)-2-(trimethylsilyl)cyclopropane (trans)-1-(2-phenylethyl)-1-(methanesulfonyloxy)-2-(trimethylsilyl)cyclopropane was obtained using 3-phenylpropionic acid methyl ester in accordance with the method disclosed in Preparation Example 1. The results of $^1$H-NMR and $^{13}$C-NMR are given below:

$^1$H-NMR (CDCl$_3$, δ): 7.18~7.33 (5H, m), 2.87~3.04 (2H, m), 2.932 (3H, s), 2.585 (1H, m), 1.719 (1H, m), 1.308 (1H, ddd), 0.716 (1H, dd), 0.440 (1H, dd), 0.000 (9H, s).

$^{13}$C-NMR (CDCl$_3$, δ): 141.367, 128.447, 128.395, 125.954, 70.696, 39.770, 37.015, 32.480, 14.921, 12.843, −1.194.

Preparation Example 3

Synthesis of (trans)-1-(3-phenylpropyl)-1-(methanesulfonyloxy)-2-(trimethylsilyl)cyclopropane (trans)-1-(3-phenylpropyl)-1-(methanesulfonyloxy)-2-(trimethylsilyl) was obtained using 4-phenylbutanoic acid methyl ester in accordance with the method disclosed in Preparation Example 1. The results of $^1$H-NMR and $^{13}$C-NMR are given below:

$^1$H-NMR (CDCl$_3$, δ): 7.26~7.31 (2H, m), 7.15~7.20 (3H, m), 2.900 (3H, s), 2.677 (2H, t), 2.186 (1H, m), 1.85~2.06 (2H, m), 1.432 (1H, m), 1.312 (1H, ddd), 0.647 (1H, dd), 0.435 (1H, dd), −0.003 (9H, s).

$^{13}$C-NMR (CDCl$_3$, δ): 141.878, 128.411, 128.368, 125.894, 71.191, 39.895, 35.389, 34.427, 27.865, 14.914, 12.999, −1.287.

Preparation Example 4

Synthesis of (trans)-1-(4-phenylbutyl)-1-(methanesulfonyloxy)-2-(trimethylsilyl)cyclopropane (trans)-1-(4-phenylbutyl)-1-(methanesulfonyloxy)-2-(trimethylsilyl)cyclopropane was obtained using 5-phenylpentanoic acid methyl ester in accordance with the method disclosed in Preparation Example 1. The results of $^1$H-NMR and $^{13}$C-NMR are given below:

$^1$H-NMR (CDCl$_3$, δ): 7.26~7.31 (2H, m), 7.15~7.21 (3H, m), 2.895 (3H, s), 2.646 (2H, t), 2.183 (1H, m), 1.62~1.76 (4H, m), 1.460 (1H, m), 1.317 (1H, ddd), 0.654 (1H, dd), 0.481 (1H, dd), 0.053 (9H, s).

$^{13}$C-NMR (CDCl$_3$, δ): 142.298, 128.393, 128.282, 125.714, 71.189, 39.866, 35.779, 34.893, 31.114, 25.718, 15.057, 12.778, −1.187.

Preparation Example 5

Synthesis of (trans)-1-(5-phenylpentyl)-1-(methansulfonyloxy)-2-(trimethylsilyl)cyclopropane (trans)-1-(5-phenylpentyl)-1-(methanesulfonyloxy)-2-(trimethylsilyl)cyclopropane was obtained using 6-phenylhexanoic acid methyl ester in accordance with the method disclosed in Preparation Example 1. The results of $^1$H-NMR and $^{13}$C-NMR are given below:

$^1$H-NMR (CDCl$_3$, δ): 7.26~7.31 (2H, m), 7.16~7.21 (3H, m), 2.945 (3H, s), 2.631 (2H, t), 2.183 (1H, m), 1.58~1.73 (4H, m), 1.35~146 (3H, m), 1.317 (1H, ddd), 0.664 (1H, dd), 0.479 (1H, dd), 0.074 (9H, s).

$^{13}$C-NMR (CDCl$_3$, δ): 142.547, 128.371, 128.235, 125.622, 71.319, 39.922, 35.816, 34.979, 31.347, 29.006, 25.997, 14.953, 12.844, −1.172.

$^{13}$C-NMR (CDCl$_3$, δ): 142.298, 128.393, 128.282, 125.714, 71.189, 39.866, 35.779, 34.893, 31.114, 25.718, 15.057, 12.778, −1.187.

Preparation Example 6

Synthesis of (trans)-1-(3-phenoxypropyl)-1-(methanesulfonyloxy)-2-(trimethylsilyl)cyclopropane (trans)-1-(3-phenoxypropyl)-1-(methanesulfonyloxy)-2-(trimethylsilyl)cyclopropane was obtained using 4-phenoxybutanoic acid methyl ester in accordance with the method disclosed in Preparation Example 1. The results of $^1$H-NMR and $^{13}$C-NMR are given below:

$^1$H-NMR (CDCl$_3$, δ): 7.277 (2H, m), 6.956 (1H, m), 6.867 (2H, m), 4.040 (2H, m), 2.971 (3H, s), 2.382 (1H, m), 2.04~2.21 (2H, m), 1.700 (1H, m), 1.336 (1H, ddd), 0.693 (1H, dd), 0.540 (1H, dd), 0.093 (9H, s).

$^{13}$C-NMR (CDCl$_3$, δ): 158.761, 129.420, 120.624, 114.340, 70.745, 66.495, 39.926, 31.378, 26.000, 14.914, 12.903, −1.237.

Preparation Example 7

Synthesis of (trans)-1-(4-phenoxybutyl)-1-(methanesulfonyloxy)-2-(trimethylsilyl)cyclopropane (trans)-1-(4-phenoxybutyl)-1-(methanesulfonyloxy)-2-(trimethylsilyl)cyclopropane was obtained using 5-phenoxypentanoic acid methyl ester in accordance with the method disclosed in Preparation Example 1. The results of $^1$H-NMR and $^{13}$C-NMR are given below:

$^1$H-NMR (CDCl$_3$, δ): 7.275 (2H, m), 6.894 (1H, m), 6.867 (2H, m), 3.989 (2H, t), 2.952 (3H, s), 2.258 (1H, m), 1.77~1.92 (4H, m), 1.511 (1H, m), 1.347 (1H, ddd), 0.679 (1H, dd), 0.520 (1H, dd), 0.083 (9H, s).

$^{13}$C-NMR (CDCl$_3$, δ): 158.926, 129.402, 120.564, 114.426 71.101, 67.451, 39.916, 34.768, 28.958, 22.840, 15.045, 12.846, −1.185.

Preparation Example 8

Synthesis of (trans)-1-pentyl-1-(methanesulfonyloxy)-2-(trimethylsilyl)cyclopropane (trans)-1-pentyl-1-(methanesulfonyloxy)-2-(trimethylsilyl)cyclopropane was obtained using hexanoic acid methyl ester in accordance with the method disclosed in Preparation Example 1. The results of $^1$H-NMR and $^{13}$C-NMR are given below:

$^1$H-NMR (CDCl$_3$, δ): 2.955 (3H, s), 2.152 (1H, m), 1.2~1.5 (8H, broad m), 0.903 (3H, t), 0.652 (1H, dd), 0.485 (1H, dd), 0.066 (9H, s).

$^{13}$C-NMR (CDCl$_3$, δ): 71.469, 39.948, 34.988, 31.586, 25.844, 22.596, 14.961, 14.012, 12.842, −1.182

Preparation Example 9

Synthesis of (trans)-1-hexyl-1-(methanesulfonyloxy)-2-(trimethylsilyl)cyclopropane (trans)-1-hexyl-1-(methanesulfonyloxy)-2-(trimethylsilyl)cyclopropane was obtained using heptanoic acid methyl ester in accordance with the method disclosed in Preparation Example 1. The results of $^1$H-NMR and $^{13}$C-NMR are given below:

$^1$H-NMR (CDCl$_3$, δ): 2.955 (3H, s), 2.148 (1H, m), 1.2~1.5 (10H, broad m), 0.888 (3H, t), 0.653 (1H, dd), 0.485 (1H, dd), 0.068 (9H, s).

$^{13}$C-NMR (CDCl$_3$, δ): 71.495, 39.959, 35.049, 31.750, 29.081, 26.126, 22.579, 14.973, 14.034, 12.872, −1.176

Preparation Example 10

Synthesis of (trans)-1-octyl-1-(methanesulfonyloxy)-2-(trimethylsilyl)cyclopropane (trans)-1-octyl-1-(methanesulfonyloxy)-2-(trimethylsilyl) cyclopropane was obtained using nonanoic acid methyl ester in accordance with the method disclosed in Preparation Example 1. The results of $^1$H-NMR and $^{13}$C-NMR are given below:

$^1$H-NMR (CDCl$_3$, δ): 2.946 (3H, s), 2.143 (1H, m), 1.53~1.65 (2H, b), 1.403 (1H, m), 1.23~1.35 (11H, broad m), 0.871 (3H, t), 0.645 (1H, dd), 0.476 (1H, dd), 0.060 (9H, s).

$^{13}$C-NMR (CDCl$_3$, δ): 71.453, 39.959, 39.923, 35.007, 31.799, 29.494, 29.385, 29.202, 26.132, 22.617, 14.941, 14.059, 12.822, −1.203

Preparation Example 11

Synthesis of (trans)-1-(4-methoxybenzyl)-1-(methanesulfonyloxy)-2-(trimethylsilyl)cyclopropane 2.02 g of magnesium and 30 ml of ethyl ether were placed in a 100 ml three-neck round bottom flask and 6.3 g of 2-chloropropane was slowly added thereto to prepare a Grignard solution. Meanwhile, 10.7 g of titanium (IV) isopropoxide, 3.7 g of vinyltrimethylsilane and 5.5 g of 4-methoxyphenylacetic acid methyl ester were placed in another 100 ml three-neck round bottom flask at −35° C., and the above-prepared Grignard solution was slowly added thereto for 30 minutes. The reaction solution was further vigorously stirred for 3 hours, while being kept at 35° C. The reaction solution was cooled to 0° C. and 7 ml of concentrated brine was added to the solution. The resulting solution was filtered through Celite which was then thoroughly washed once more with 20 ml of ether. The filtrate thus obtained was dried over anhydrous magnesium sulfate (MgSO$_4$) and was concentrated by the evaporation of solvent at a low temperature of 30° C. or less. (trans)-1-(4-methoxybenzyl)-1-hydroxy-2-(trimethylsilyl)cyclopropane was purely separated from the resulting product using silica gel. The results of $^1$H-NMR and $^{13}$C-NMR are given below.

$^1$H-NMR (DMSO-d$_6$, δ): 7.211 (2H, d, J=1.6, 8.8 Hz), 6.832 (2H, d, J=8.8 Hz), 5.154 (1H, s), 3.716 (3H, s), 2.928 (1H, d, J=14.4 Hz), 2.460 (1H, d, J=14.4 Hz), 0.805 (1H, ddd, J=1.2, 4.0, 11.2 Hz), 0.481 (1H, dd, J=4.0, 8.4 Hz), 0.000 (9H, s), −0.048 (1H, dd, J=4.0, 8.4 Hz).

$^{13}$C-NMR (DMSO-d$_6$, δ): 157.975, 132.544, 130.655, 113.717, 59.102, 55.430, 41.986, 17.087, 14.124, −0.156.

2.8 g of the alcohol compound obtained above was dissolved in 15 ml of dichloromethane and 2.5 ml of triethylamine was added thereto. The reaction solution was cooled to 0° C., 1.5 g of methansulfonyl chloride was slowly added thereto and the reaction solution was then vigorously stirred for one hour. 10 ml of NaHCO$_3$ was added to the reaction solution to complete the reaction. An organic layer was separated from the resulting reaction, concentrated and purified to obtain (trans)-1-(4-methoxybenzyl)-1-(methanesulfonyloxy)-2-(trimethylsilyl)cyclopropane. The $^1$H-NMR and $^{13}$C-NMR data for the product are given below.

$^1$H-NMR (CDCl$_3$, δ): 7.275 (2H, d, J=8.8 Hz), 6.871 (2H, d, J=8.8 Hz), 3.804 (3H, s), 3.650 (1H, d, J=15.6 Hz), 2.776 (3H, s), 2.579 (1H, d, J=15.6 Hz), 1.371 (1H, ddd, J=1.6, 5.2, 12.4 Hz), 0.901 (1H, dd, J=9.6, 12.4 Hz), 0.744 (1H, dd, J=5.2, 9.6 Hz), 0.127 (9H, s).

$^{13}$C-NMR (CDCl$_3$, δ): 158.385, 130.073, 129.584, 70.406, 55.198, 39.756, 39.500, 15.154, 12.769, −1.170.

Preparation Example 12

Synthesis of (trans)-1-(2-(4-methoxyphenyl)ethyl)-1-(methanesulfonyloxy)-2-(trimethylsilyl)cyclopropane (trans)-1-(2-(4-methoxyphenyl)ethyl)-1-(methane sulfonyloxy)-2-(trimethylsilyl)cyclopropane was obtained using 3-(4-methoxyphenyl)propionic acid methyl ester in accordance with the method disclosed in Preparation Example 11. The results of $^1$H-NMR and $^{13}$C-NMR are given below:

$^1$H-NMR (CDCl$_3$, δ): 7.128 (2H, d, J=8.8 Hz), 6.834 (2H, d, J=8.8 Hz), 3.788 (3H, s), 2.946 (3H, s), 2.876 (1H, m), 2.535 (1H, m), 1.662 (1H, m), 1.280 (1H, m), 0.688 (1H, dd), 0.419 (1H, dd), 0.068 (9H, s).

$^{13}$C-NMR (CDCl$_3$, δ): 157.834, 133.402, 129.346, 113.773, 70.747, 55.216, 39.830, 37.262, 31.522. 14.947, 12.772, −1.232.

Preparation Example 13

Synthesis of (trans)-1-(3-(4-methoxyphenyl)propyl)-1-(methanesulfonyloxy)-2-(trimethylsilyl)cyclopropane (trans)-1-(3-(4-methoxyphenyl)propyl)-1-(methanesulfonyloxy)-2-(trimethylsilyl)cyclopropane was obtained using 4-(4-methoxyphenyl)butanoic acid methyl ester in accordance with the method disclosed in Preparation Example 11. The results of $^1$H-NMR and $^{13}$C-NMR are given below:

$^1$H-NMR (CDCl$_3$, δ): 7.096 (2H, d, J=8.8 Hz), 6.823 (2H, d, J=8.8 Hz), 3.781 (3H, s), 2.906 (3H, s), 2.616 (2H, t), 2.172 (1H, m), 1.82~2.03 (2H, m), 1.425 (1H, m), 1.311 (1H, m), 0.645 (1H, dd), 0.437 (1H, dd), 0.005 (9H, s).

$^{13}$C-NMR (CDCl$_3$, δ): 157.745, 133.920, 129.247, 113.722, 71.183, 55.236, 39.865, 34.434, 34.335, 28.077, 14.881, 12.919, −1.291.

Preparation Example 14

Synthesis of 1-benzylcyclopropene 2.95 g of (trans)-1-benzyl-1-(methanesulfonyloxy)-2-(trimethylsilyl)cyclopropane prepared in Preparation Example 1 was dissolved in 20 ml of DMF, 4.6 g of Bu$_4$NF.3H$_2$O was added thereto, and the resulting mixture was vigorously stirred at room temperature for one hour. 10 ml of pentane and 10 ml of water were added to the reaction solution, vigorously shaken and stood. When the mixture was separated into a pentane layer (upper layer) and an aqueous layer (lower layer), the pentane layer was collected and immediately concentrated by distillation under vacuum at 20° C. or below. At this time, the pentane layer was separated from the mixture, concentrated without any additional purification process and subjected to $^1$H-NMR and $^{13}$C-NMR for confirmation of structure within one hour. 1-benzylcyclopropene was present in a mixture with a decomposed product. $^1$H-NMR and $^{13}$C-NMR for the product are given below.

$^1$H-NMR (CDCl$_3$, δ): 7.22~7.38 (5H, m), 6.603 (1H, m, J=1.6 Hz), 3.850 (2H, s), 1.029 (2H, d, J=1.6).

$^{13}$C-NMR (CDCl$_3$, δ): 137.758, 128.480, 126.347, 124.269, 119.347, 99.399, 33.149, 6.048.

Preparation Example 15

Synthesis of 1-(2-phenylethyl)cyclopropene 1-(2-phenylethyl)cyclopropene was obtained using (trans)-1-(2-phenylethyl)-1-(methanesulfonyloxy)-2-(trimethylsilyl)cyclopropane of Preparation Example 2 by the method disclosed in Preparation Example 14. The results of $^1$H-NMR and $^{13}$C-NMR are given below:

$^1$H-NMR (CDCl$_3$, δ): 7.18~7.34 (5H, m), 6.510 (1H, m, J=1.2, 2.0 Hz), 2.951 (2H, t, J=6.4 Hz), 2.845 (2H, m, J=1.2, 6.4 Hz), 0.972 (2H, d, J=2.0 Hz).

$^{13}$C-NMR (CDCl$_3$, δ): 141.525, 128.378, 128.312, 126.016, 119.931, 98.688, 33.272, 28.626, 5.419.

Preparation Example 16

Synthesis of 1-(3-phenylpropyl)cyclopropene 1-(2-phenylethyl)cyclopropene was obtained using (trans)-1-(3-phenylpropyl)-1-(methanesulfonyloxy)-2-(trimethylsilyl)cyclopropane of Preparation Example 3 by the method disclosed in Preparation Example 14. The results of $^1$H-NMR and $^{13}$C-NMR are given below:

$^1$H-NMR (CDCl$_3$, δ): 7.28~7.34 (2H, m), 7.18~7.23 (3H, m), 6.519 (1H, m, J=1.2, 2.0 Hz), 2.704 (2H, t, J=7.6 Hz), 2.545 (2H, m, J=1.2, 7.2 Hz), 1.956 (2H, m, J=7.2, 7.6 Hz), 0.952 (2H, d, J=2.0 Hz).

$^{13}$C-NMR (CDCl$_3$, δ): 142.087, 128.476, 128.303, 125.780, 120.251, 98.168, 35.292, 28.716, 26.048, 5.138.

Preparation Example 17

Synthesis of 1-(4-phenylbutyl)cyclopropene 1-(4-phenylbutyl)cyclopropene was obtained using (trans)-1-(3-phenylbutyl)-1-(methanesulfonyloxy)-2-(trimethylsilyl)cyclopropane of Preparation Example 4 by the method disclosed in Preparation Example 14. The results of $^1$H-NMR and $^{13}$C-NMR are given below:

$^1$H-NMR (CDCl$_3$, δ): 7.24~7.29 (2H, m), 7.14~7.19 (3H, m), 6.417 (1H, m, J=1.2, 2.0 Hz), 2.609 (2H, t, J=7.6 Hz), 2.473 (2H, m, J=1.2, 7.6 Hz), 0.881 (2H, d, J=2.0 Hz).

$^{13}$C-NMR (CDCl$_3$, δ): 142.497, 128.374, 128.258, 125.662, 120.384, 97.894, 35.679, 30.963, 26.589, 26.465, 5.167.

Preparation Example 18

Synthesis of 1-(5-phenylpentyl)cyclopropene 1-(5-phenylpentyl)cyclopropene was obtained using (trans)-1-(3-phenylbutyl)-1-(methanesulfonyloxy)-2-(trimethylsilyl)cyclopropane of Preparation Example 5 by the method disclosed in Preparation Example 14. The results of $^1$H-NMR and $^{13}$C-NMR are given below:

$^1$H-NMR (CDCl$_3$, δ): 7.24~7.29 (2H, m), 7.14~7.22 (3H, m), 6.417 (1H, m, J=1.2, 2.0 Hz), 2.609 (2H, t, J=7.6 Hz), 2.473 (2H, m, J=1.2, 7.2 Hz), 1.58-1.68 (4H, m), 1.35~1.44 (2H, m), 0.876 (2H, d, J=2.0 Hz).

$^{13}$C-NMR (CDCl$_3$, δ): 142.687, 128.374, 128.229, 125.604, 120.535, 97.734, 35.835, 31.202, 28.841, 26.807, 26.545, 5.140.

Preparation Example 19

Synthesis of 1-(3-phenoxypropyl)cyclopropene 1-(3-phenoxypropyl)cyclopropene was obtained using (trans)-1-(3-phenoxypropyl)-1-(methanesulfonyloxy)-2-(trimethylsilyl)cyclopropane of Preparation Example 6 by the method disclosed in Preparation Example 14. The results of $^1$H-NMR and $^{13}$C-NMR are given below.

$^1$H-NMR (CDCl$_3$, δ): 7.23~7.30 (2H, m), 6.88~6.95 (3H, m), 6.505 (1H, m, J=1.2, 1.6 Hz), 4.006 (2H, t, J=6.4 Hz), 2.682 (2H, m, J=1.2, 7.2 Hz), 2.082 (2H, m, J=6.4, 7.2 Hz), 0.928 (2H, d, J=1.6 Hz).

$^{13}$C-NMR (CDCl$_3$, δ): 158.955, 129.411, 120.594, 119.765, 114.472, 98.590, 66.849, 26.841, 23.293, 5.269.

Preparation Example 20

Synthesis of 1-(4-phenoxybutyl)cyclopropene 1-(3-phenoxypropyl)cyclopropene was obtained using a mixture of (trans) and (cis)-1-(3-phenoxybutyl)-1-(methanesulfonyloxy)-2-(trimethylsilyl)cyclopropane of Preparation Example 7 in accordance with the method disclosed in Preparation Example 14. The results of $^1$H-NMR and $^{13}$C-NMR are given below:

$^1$H-NMR (CDCl$_3$, δ): 7.23~7.30 (2H, m), 6.87~6.95 (3H, m), 6.473 (1H, m, J=1.2, 2.0 Hz), 3.975 (2H, t, J=6.4 Hz), 2.562 (2H, m, J=1.2, 7.6 Hz), 1.72~1.88 (4H, m), 0.908 (2H, d, J=2.0 Hz).

$^{13}$C-NMR (CDCl$_3$, δ): 159.006, 129.396, 120.518, 120.182, 114.455, 98.218, 67.427, 28.788, 26.326, 23.579, 5.169.

Preparation Example 21

Synthesis of 1-pentylcyclopropene 1-pentylcyclopropene was obtained using (trans)-1-pentyl-1-(methanesulfonyloxy)-2-(trimethylsilyl)cyclopropane of Preparation Example 8 in accordance with the method disclosed in Preparation Example 14. However, this product was evaporated together with the solvent due to high volatility, while pentane was evaporated and concentrated, and was thus difficult to purely purify.

Preparation Example 22

Synthesis of 1-hexylcyclopropene 1-hexylcyclopropene was obtained using (trans)-1-hexyl-1-(methanesulfonyloxy)-2-(trimethylsilyl)cyclopropane of Preparation Example 9 in accordance with the method disclosed in Preparation Example 14. The results of $^1$H-NMR and $^{13}$C-NMR are given below.

$^1$H-NMR (CDCl$_3$, δ): 6.426 (1H, m, J=1.2, 2.0 Hz), 2.472 (2H, dt, J=1.2, 7.2 Hz), 1.579 (2H, m, J=7.6 Hz), 1.25~1.38 (6H, m), 0.889 (3H, t, J=7.2 Hz), 0.879 (2H, d, J=2.0 Hz).

$^{13}$C-NMR (CDCl$_3$, δ): 120.727, 97.560, 31.618, 28.919, 26.924, 26.647, 22.584, 14.052, 5.115.

Preparation Example 23

Synthesis of 1-octylcyclopropene 1-octylcyclopropene was obtained using (trans)-1-octyl-1-(methanesulfonyloxy)-2-(trimethylsilyl)cyclopropane of Preparation Example 10 in accordance with the method disclosed in Preparation Example 14. The results of $^1$H-NMR and $^{13}$C-NMR are given below.

$^1$H-NMR (CDCl$_3$, δ): 6.425 (1H, m, J=1.2, 2.0 Hz), 2.470 (2H, dt, J=1.2, 7.2 Hz), 1.578 (2H, m, J=7.6 Hz), 1.23~1.38 (10H, m), 0.882 (3H, t, J=6.8 Hz), 0.878 (2H, d, J=2.0 Hz).

$^{13}$C-NMR (CDCl$_3$, δ): 120.726, 97.561, 31.875, 29.385, 29.264, 26.973, 26.654, 22.680, 14.104, 5.124.

Preparation Example 24

Synthesis of 1-(4-methoxybenzyl)cyclopropene 1-(4-methoxybenzyl)cyclopropene was obtained using (trans)-1-(4-methoxybenzyl)-1-(methanesulfonyloxy)-2-(trimethylsilyl)cyclopropane prepared in Preparation Example 11 in accordance with the method disclosed in Preparation Example 14. The results of $^1$H-NMR and $^{13}$C-NMR are given below.

$^1$H-NMR (CDCl$_3$, δ): 7.123 (2H, d, J=8.4 Hz), 6.803 (2H, d, J=8.4 Hz), 6.513 (1H, m, J=1.2 Hz), 3.753 (3H, s), 3.730 (2H, s), 0.947 (2H, d, J=2.0 Hz).

$^{13}$C-NMR (CDCl$_3$, δ): 158.081, 130.753, 129.006, 127.246, 119.233, 98.611, 54.637, 31.863, 5.619.

Preparation Example 25

Synthesis of 1-(2-(4-methoxyphenyl)ethyl)cyclopropene 1-(2-(4-methoxy)phenylethyl)cyclopropene was obtained using (trans)-1-(2-(4-methoxyphenyl)ethyl)-1-(methanesulfonyloxy)-2-(trimethylsilyl)cyclopropane of Preparation Example 12 in accordance with the method disclosed in Preparation Example 14. The results of $^1$H-NMR and $^{13}$C-NMR are given below.

$^1$H-NMR (CDCl$_3$, δ): 7.075 (2H, d, J=8.8 Hz), 6.778 (2H, d, J=8.8 Hz), 6.412 (1H, m, J=1.2 Hz), 3.731 (3H, s), 2.799 (2H, t, J=6.8 Hz), 2.715 (2H, t, J=6.8 Hz), 0.866 (2H, d, J=1.2 Hz).

$^{13}$C-NMR (CDCl$_3$, δ): 157.633, 133.381, 129.080, 119.734, 113.484, 98.376, 54.967, 32.149, 28.700, 5.186.

Preparation Example 26

Synthesis of 1-(3-(4-methoxyphenyl)propyl)cyclopropene 1-(3-(4-methoxyphenyl)propyl)cyclopropene was obtained using (trans)-1-(3-(4-methoxyphenyl)propyl)-1-(methanesulfonyloxy)-2-(trimethylsilyl)cyclopropane of Preparation Example 13 in accordance with the method disclosed in Preparation Example 14. The results of $^1$H-NMR and $^{13}$C-NMR are given below.

$^1$H-NMR (CDCl$_3$, δ): 7.096 (2H, d, J=8.8 Hz), 6.827 (2H, d, J=8.8 Hz), 6.477 (1H, m, J=1.2 Hz), 3.778 (3H, s), 2.608 (2H, t, J=7.2 Hz), 2.492 (2H, t, J=6.8 Hz), 1.879 (2H, t, J=6.8, 7.2 Hz), 0.911 (2H, d, J=1.2 Hz).

$^{13}$C-NMR (CDCl$_3$, δ): 157.614, 134.002, 129.232, 120.138, 113.574, 97.959, 55.084, 34.216, 28.828, 25.833, 5.037.

1-alkylcyclopropenes of Formula 1 illustrated in Preparation Examples 14 to 26 exhibited low stability and could not be thus easily stored for a long period of time. Accordingly, the cyclopropenes prepared herein were synthesized and at the same time was immediately formulated using a surfactant. It is more convenient when the 1-alkylcyclopropenes are formulated by dissolving the same in a solvent such as pentane, hexane, benzene, toluene, xylene, mesitylene and ethylbenzene, since they were pure hydrocarbon compounds. The surfactants used herein may be any of cationic and anionic surfactants and anionic surfactants are generally more economical and convenient. Hereinafter, the formulation process will be described in more detail with reference to Examples 1 to 6. These examples are provided only to illustrate the process and should not be construed as limiting the scope and spirit of the present invention.

Example 1

Preparation of 1-(3-phenylpropyl)cyclopropene formulation

In situ, 0.660 g (2.0 mmol) of (trans)-1-(3-phenylpropyl)-1-(methanesulfonyloxy)-2-(trimethylsilyl)cyclopropane of Preparation Example 3 was dissolved in 2.0 ml of DMSO, 0.94 g of Bu$_4$NF.3H$_2$O was added thereto and the resulting mixture was vigorously stirred at room temperature for one hour. 8.0 ml of toluene and 5.0 ml of water were added to the reaction solution and vigorously stirred for 5 minutes and stood. When the mixture was separated into a toluene layer (upper layer) and an aqueous layer (lower layer), only the toluene layer was collected and the aqueous layer was discarded. 1.0 g of sodium dodecylbenzenesulfonate and 1.0 g of tristyrenylphenykethoxy)$_{12}$ethanol were added to the toluene layer, stirred for 5 minutes, 2.0 L of water was added thereto and the resulting mixture was slowly stirred such that it was homogeneously mixed. As a result, a 1.0 mM 1-(3-phenylpropyl)cyclopropene formulation was prepared. This solution was diluted 1 to 100 times prior to use, as necessary.

Example 2

Preparation of 1-(2-phenylethyl)cyclopropene formulation

In situ, a 1.0 mM 1-(2-phenylethyl)cyclopropene formulation was prepared using (trans)-1-(2-phenylethyl)-1-(methane sulfonyloxy)-2-(trimethylsilyl)cyclopropane of Preparation Example 2 in the same manner as in Example 1. This solution was diluted to 1 to 100 times prior to use, as necessary.

Example 3

Preparation of 1-(4-phenylbutyl)cyclopropene formulation

In situ, a 1.0 mM 1-(2-phenylbutyl)cyclopropene formulation was prepared using (trans)-1-(4-phenylbutyl)-1-(methanesulfonyloxy)-2-(trimethylsilyl)cyclopropane of Preparation Example 4 in the same manner as in Example 1. This solution was diluted to 1 to 100 times prior to use, as necessary.

Example 4

Preparation of 1-(5-phenylpentyl)cyclopropene formulation

In situ, 0.718 g (2.0 mmol) of (trans)-1-(5-phenylpentyl)-1-(methanesulfonyloxy)-2-(trimethylsilyl)cyclopropane of Preparation Example 5 was dissolved in 2.0 ml of DMSO, 0.94 g of $Bu_4NF.3H_2O$ was added thereto and the resulting mixture was vigorously stirred at room temperature for one hour. 8.0 ml of xylene and 5.0 ml of water were added to the reaction solution and vigorously stirred for 5 minutes and stood. When the mixture was separated into a xylene layer (upper layer) and an aqueous layer (lower layer), only the xylene layer was collected and the aqueous layer was discarded. 1.0 g of sodium dodecylbenzenesulfonate and 1.0 g of tristyrenylphenykethoxy)$_{12}$ethanol were added to the xylene layer, stirred for 5 minutes, 2.0 L of water was added thereto and the resulting mixture was slowly stirred such that it was homogeneously mixed. As a result, a 1.0 mM 1-(5-phenylpentyl)cyclopropene formulation was prepared. This solution was diluted to 1 to 100 times prior to use, as necessary.

Example 5

Preparation of 1-(3-phenoxypropyl)cyclopropene formulation

In situ, 0.688 g (2.0 mmol) of (trans)-1-(3-phenoxypropyl)-1-(methanesulfonyloxy)-2-(trimethylsilyl)cyclopropane of Preparation Example 6 was dissolved in 2.0 ml of DMSO, 0.94 g of $Bu_4NF.3H_2O$ was added thereto and the resulting mixture was vigorously stirred at room temperature for one hour. 6.0 ml of xylene and 5.0 ml of water were added to the reaction solution and vigorously stirred for 5 minutes and stood. When the mixture was separated into a xylene layer (upper layer) and an aqueous layer (lower layer), only the xylene layer was collected and the aqueous layer was discarded. 1.0 g of sodium dodecylbenzenesulfonate and 1.0 g of Triton® X-100 were added to the xylene layer, stirred for 5 minutes, 2.0 L of water was added thereto and the resulting mixture was slowly stirred such that it was homogeneously mixed. As a result, a 1.0 mM 1-(5-phenylpentyl)cyclopropene formulation was prepared. This solution was diluted to 1 to 100 times prior to use, as necessary.

Example 6

Preparation of 1-(4-phenoxybutyl)cyclopropene formulation

In situ, 0.715 g (2.0 mmol) of (trans)-1-(4-phenoxybutyl)-1-(methanesulfonyloxy)-2-(trimethylsilyl)cyclopropane of Preparation Example 7 was dissolved in 3.0 ml of DMSO, 0.94 g of $Bu_4NF.3H_2O$ was added thereto and the resulting mixture was vigorously stirred at room temperature for one hour. 8.0 ml of toluene and 5.0 ml of water were added to the reaction solution and vigorously stirred for 5 minutes and stood. When the mixture was separated into a toluene layer (upper layer) and an aqueous layer (lower layer), only the toluene layer was collected and the aqueous layer was discarded. 1.0 g of sodium dodecylbenzenesulfonate and 1.0 g of tristyrenylphenyl(ethoxy)$_{12}$ ethanol were added to the toluene layer, stirred for 5 minutes, 2.0 L of water was added thereto and the resulting mixture was slowly stirred such that it was homogeneously mixed. As a result, a 1.0 mM 1-octylcyclopropene formulation was prepared. This solution was diluted to 1 to 100 times prior to use, as necessary.

Example 7

Preparation of 1-hexylcyclopropene formulation

In situ, 0.586 g (2.0 mmol) of (trans)-1-hexyl-1-(methane sulfonyloxy)-2-(trimethylsilyl)cyclopropane of Preparation Example 9 was dissolved in 2.0 ml of DMSO, 0.94 g of $Bu_4NF.3H_2O$ was added thereto and the resulting mixture was vigorously stirred at room temperature for one hour. 8.0 ml of xylene and 5.0 ml of water were added to the reaction solution and vigorously stirred for 5 minutes and stood. When the mixture was separated into a xylene layer (upper layer) and an aqueous layer (lower layer), only the xylene layer was collected and the aqueous layer was discarded. 1.0 g of sodium dodecylbenzenesulfonate and 1.0 g of tristyrenylphenykethoxy)$_{12}$ethanol were added to the xylene layer, stirred for 5 minutes, 2.0 L of water was added thereto and the resulting mixture was slowly stirred such that it was homogeneously mixed. As a result, a 1.0 mM 1-hexylcyclopropene formulation was prepared. This solution was diluted to 1 to 100 times prior to use, as necessary.

Example 8

Preparation of 1-octylcyclopropene Formulation

In situ, a 1.0 mM 1-octylcyclopropene formulation was prepared using (trans)-1-octyl-1-(methanesulfonyloxy)-2-(trimethylsilyl)cyclopropane of Preparation Example 10 in the same manner as in Example 7. This solution was diluted to 1 to 100 times prior to use, as necessary. Experimental Example 1: Efficacy test on tomato using emulsion 1.0 mM formulations of five agents such as 1-(2-phenylethyl)cyclopropene, 1-(3-phenylpropyl)cyclopropene, 1-(4-phenylbutyl)cyclopropene, 1-(5-phenylpentyl)cyclopropene and 1-hexylcyclopropene were prepared in the same manner as in Example 1, and 1.0 mM and 100 µM solutions were prepared therefrom. Then, the effects of the solutions were compared with non-treated groups and control groups in which a surfactant or a stabilizing agent (sodium dodecylbenzenesulfonate or tristyrenylphenykethoxy)$_{12}$ethanol) is dissolved.

Tomatoes whose top end began to turn pink were screened, harvested and divided into 12 groups (n=4) in total, i.e., non-treated groups, control groups (surfactant) and agent groups with different concentrations such as 100 μM and 1.0 mM. Tomatoes were treated with the prepared agent formulation using a household sprayer such that the surface thereof was saturated. The tomatoes were stood at room temperature (25-30° C.) for 3 days and a reddening level thereof was evaluated based on grades of 0 to 5.

At this time, the tops of tomatoes most early turned red, while the bottoms thereof most lately turned red. For this reason, in order to accurately evaluate the difference in reddening, the coloring evaluated was based on the area of red color, rather than the color of tomatoes. That is, when an area in which the surface of tomato was colored in pink was 10% or less, the grade was assigned to '0', when an area in which the surface of tomato was completely colored in red was 10 to 40%, the grade was assigned to '1', when an area in which the surface of tomato was completely colored in red was 40 to 70%, the grade was assigned to '2', when an area in which the surface of tomato was completely colored in red was 70% or more and the bottom area remained green, the grade was assigned to '3', when an area in which the surface of tomato was most colored in red and only a part of (0 to 10%) the bottom area remained green, the grade was assigned to '4', and when the surface of tomato did not entirely color in green, the grade was assigned to '5'. Accordingly, the grade level is proportional to the rate at which the tomatoes ripened. Test results are shown in Table 2 below.

TABLE 2

| 1-(alkyl)cyclopropene | Days | Treatment concentration (100 μM) | | | | Treatment concentration (1.0 mM) | | | |
|---|---|---|---|---|---|---|---|---|---|
| Non-treated group | Day 0 | 0 | 0 | 1 | 2 | — | — | — | — |
| | Day 1 | 1 | 2 | 3 | 4 | — | — | — | — |
| | Day 2 | 3 | 4 | 4 | 5 | — | — | — | — |
| | Day 3 | 5 | 5 | 5 | 5 | — | — | — | — |
| Control group | Day 0 | 0 | 0 | 1 | 2 | — | — | — | — |
| | Day 1 | 2 | 2 | 3 | 4 | — | — | — | — |
| | Day 2 | 4 | 4 | 4 | 5 | — | — | — | — |
| | Day 3 | 5 | 5 | 5 | 5 | — | — | — | — |
| (2-Phenylethyl) | Day 0 | 0 | 0 | 1 | 2 | 0 | 0 | 1 | 2 |
| | Day 1 | 1 | 1 | 3 | 3 | 1 | 1 | 2 | 3 |
| | Day 2 | 2 | 3 | 4 | 4 | 2 | 2 | 3 | 4 |
| | Day 3 | 3 | 4 | 5 | 5 | 3 | 3 | 4 | 5 |
| (3-Phenylpropyl) | Day 0 | 0 | 0 | 1 | 2 | 0 | 0 | 1 | 2 |
| | Day 1 | 1 | 1 | 1 | 2 | 0 | 0 | 1 | 2 |
| | Day 2 | 1 | 1 | 2 | 3 | 1 | 0 | 1 | 3 |
| | Day 3 | 2 | 2 | 3 | 4 | 1 | 1 | 2 | 3 |
| (4-Phenylbutyl) | Day 0 | 0 | 0 | 1 | 2 | 0 | 0 | 1 | 2 |
| | Day 1 | 0 | 0 | 1 | 2 | 0 | 0 | 1 | 2 |
| | Day 2 | 1 | 1 | 2 | 3 | 0 | 0 | 1 | 3 |
| | Day 3 | 2 | 2 | 3 | 4 | 1 | 1 | 2 | 3 |
| (5-Phenylpentyl) | Day 0 | 0 | 0 | 1 | 2 | 0 | 0 | 1 | 2 |
| | Day 1 | 0 | 0 | 2 | 2 | 0 | 0 | 1 | 2 |
| | Day 2 | 0 | 1 | 3 | 3 | 0 | 0 | 1 | 2 |
| | Day 3 | 1 | 2 | 3 | 4 | 0 | 1 | 2 | 3 |
| (Hexyl) | Day 0 | 0 | 0 | 1 | 2 | 0 | 0 | 1 | 2 |
| | Day 1 | 1 | 1 | 3 | 4 | 1 | 1 | 2 | 3 |
| | Day 2 | 3 | 3 | 4 | 5 | 2 | 2 | 3 | 4 |
| | Day 3 | 4 | 5 | 5 | 5 | 3 | 3 | 5 | 5 |

Experimental Example 2

Efficacy Test on Tomato Using Oil Based Formulation

As illustrated in Example 1, in situ, in accordance with the methods of Preparation Examples 15, 16, 17, 18 and 22, five agents (1.0 mmol) such as 1-(2-phenylethyl)cyclopropene, 1-(3-phenylpropyl)cyclopropene, 1-(4-phenylbutyl)cyclopropene, 1-(5-phenylpentyl)cyclopropene and 1-hexylcyclopropene were prepared, 5.0 ml of xylene and 5.0 ml of water were added to the reaction solution, vigorously stirred for 5 minutes and stood. When the mixture was separated into an organic layer (upper layer) and an aqueous layer (lower layer), only the organic layer was collected and the aqueous layer was discarded. 100 ml of hexane was added to the organic layer and homogeneously mixed to prepare a 1.0 mM oil-based formulation.

The tomatoes were screened in the same manner as in Experimental Example 1 and divided into 7 groups (n=4) including a non-treated group, a control group (solvent-treated group) and 5 agent groups. Tomatoes were treated with the previously prepared agent using a household sprayer such that the surface thereof was saturated. The tomatoes were stood at room temperature (25-30° C.) for 3 days and a reddening level thereof was evaluated based on grades of 0 to 5. Test results are shown in Table 3 below.

TABLE 3

| 1-(alkyl)cyclopropene | Days | Tomato results | | | |
|---|---|---|---|---|---|
| Non-treated group | Day 0 | 0 | 0 | 1 | 2 |
| | Day 1 | 3 | 2 | 3 | 4 |
| | Day 2 | 4 | 4 | 4 | 5 |
| | Day 3 | 5 | 5 | 5 | 5 |
| Control group | Day 0 | 0 | 0 | 1 | 2 |
| | Day 1 | 2 | 2 | 3 | 4 |
| | Day 2 | 4 | 4 | 4 | 5 |
| | Day 3 | 5 | 5 | 5 | 5 |
| (2-Phenylethyl) | Day 0 | 0 | 0 | 1 | 2 |
| | Day 1 | 1 | 1 | 2 | 3 |
| | Day 2 | 2 | 2 | 4 | 4 |
| | Day 3 | 4 | 4 | 5 | 5 |
| (3-Phenylpropyl) | Day 0 | 0 | 0 | 1 | 2 |
| | Day 1 | 0 | 0 | 1 | 2 |
| | Day 2 | 0 | 0 | 1 | 3 |
| | Day 3 | 1 | 1 | 2 | 4 |
| (4-Phenylbutyl) | Day 0 | 0 | 0 | 1 | 2 |
| | Day 1 | 0 | 0 | 1 | 2 |
| | Day 2 | 0 | 0 | 1 | 3 |
| | Day 3 | 1 | 0 | 2 | 4 |
| (5-Phenylpentyl) | Day 0 | 0 | 0 | 1 | 2 |
| | Day 1 | 0 | 0 | 1 | 2 |
| | Day 2 | 0 | 1 | 2 | 3 |
| | Day 3 | 1 | 1 | 3 | 4 |
| (Hexyl) | Day 0 | 0 | 0 | 1 | 2 |
| | Day 1 | 1 | 1 | 2 | 3 |
| | Day 2 | 3 | 2 | 4 | 5 |
| | Day 3 | 4 | 4 | 5 | 5 |

Experimental Example 3

Efficacy Test on Tomato for Other Drugs 1.0 mM emulsions and oil-based formulations of four agents, i.e., 1-(2-(4-methoxyphenyl)ethyl)cyclopropene, 1-(3-(4-methoxyphenyl)propyl)cyclopropene, 1-(3-phenoxypropyl)cyclopropene and 1-(4-phenoxybutyl)cyclopropene were prepared in accordance with Examples 1 and 2.

The tomatoes were screened in the same manner as in Experimental Example 1 and divided into 9 groups (n=4), i.e., a non-treated group and 4 emulsion-type agent groups and 4 oil-based formulation-type agent groups. Tomatoes were treated with the previously prepared agent using a household sprayer such that the surface thereof was saturated. The tomatoes were stood at room temperature (25-30° C.) for 3 days and a reddening level thereof was evaluated based on grades of 0 to 5. The test results are shown in Table 4 below.

TABLE 4

| 1-(alkyl)cyclopropene | Days | Emulsion | | | | Oil-based formulation | | | |
|---|---|---|---|---|---|---|---|---|---|
| Non-treated group | Day 0 | 0 | 0 | 1 | 2 | — | — | — | — |
| | Day 1 | 2 | 2 | 3 | 4 | — | — | — | — |
| | Day 2 | 4 | 4 | 5 | 5 | — | — | — | — |
| | Day 3 | 5 | 5 | 5 | 5 | — | — | — | — |
| (2-(4-Methoxy-phenyl)ethyl) | Day 0 | 0 | 0 | 1 | 2 | 0 | 0 | 1 | 2 |
| | Day 1 | 1 | 1 | 3 | 3 | 1 | 1 | 2 | 3 |
| | Day 2 | 3 | 3 | 4 | 5 | 2 | 2 | 3 | 4 |
| | Day 3 | 4 | 4 | 5 | 5 | 3 | 3 | 4 | 5 |
| (3-(4-Methoxy-phenyl)propyl) | Day 0 | 0 | 0 | 1 | 2 | 0 | 0 | 1 | 2 |
| | Day 1 | 0 | 0 | 1 | 2 | 0 | 0 | 1 | 2 |
| | Day 2 | 1 | 1 | 2 | 3 | 1 | 1 | 2 | 3 |
| | Day 3 | 2 | 2 | 3 | 4 | 1 | 2 | 3 | 3 |
| (3-Phenoxypropyl) | Day 0 | 0 | 0 | 1 | 2 | 0 | 0 | 1 | 2 |
| | Day 1 | 0 | 0 | 1 | 2 | 0 | 0 | 1 | 2 |
| | Day 2 | 1 | 1 | 2 | 2 | 0 | 0 | 2 | 3 |
| | Day 3 | 2 | 2 | 3 | 3 | 1 | 1 | 2 | 3 |
| (4-Phenoxybutyl) | Day 0 | 0 | 0 | 1 | 2 | 0 | 0 | 1 | 2 |
| | Day 1 | 0 | 0 | 2 | 2 | 0 | 0 | 1 | 2 |
| | Day 2 | 1 | 1 | 3 | 3 | 0 | 1 | 2 | 2 |
| | Day 3 | 2 | 2 | 4 | 4 | 1 | 1 | 3 | 3 |

As can be seen from Experimental Examples 1, 2 and 3, the non-treated groups and control groups began to age on the first day and were then fully ripened by about the third day 3 such that they were entirely colored in red, while the treated groups maintained to be not completely colored in red even on the third day. These results demonstrated that 1-alkylcyclopropenes prepared by the method in accordance with the present invention can efficiently block the ripening process in tomatoes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for treating plants with 1-alkylcyclopropene represented by Formula 1 below comprising:
   mixing (i) a 1-alkylcyclopropene precursor-containing agent of Formula 2 or 3 and (ii) a fluoride-containing agent, separately supplied, to prepare 1-alkylcyclopropene of Formula 1;
   simultaneously or continuously with the mixing, phase-separating 1-alkylcyclopropene of Formula 1 from the reaction solution; and
   applying the 1-alkylcyclopropene of Formula 1 to plants, wherein the steps are carried out in situ;

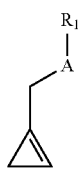
(1)

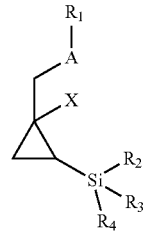
(2)

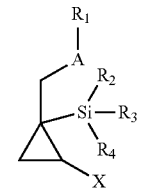
(3)

wherein A represents a straight-chain linkage having the formula of $(CH_2)_m Y(CH_2)_n$, in which m and n each independently represent an integer of 0 to 3 and Y each independently represents $CH_2$, O or S;

$R_1$ represents $C_4$-$C_{10}$ aryl, furanyl, pyranyl, or thiofuranyl, each of which may be substituted with at least one selected from the group consisting of fluoride, chloride, bromide, iodide, oxygen, sulfur, nitrogen and silicon;

$R_2$, $R_3$ and $R_4$ each independently represent saturated or unsaturated $C_1$-$C_{10}$ alkyl or alkoxy, $C_6$-$C_{10}$ aryl or aryloxy, $C_1$-$C_{10}$ primary amine or secondary amine, or halogen; and X represents halogen or $OSO_2T$, in which T represents hydrogen, saturated or unsaturated $C_1$-$C_{10}$ alkyl, alkoxy or aryl, aryloxy, amine, halogen or hydroxy.

2. The method according to claim 1, wherein $R_1$ represents $C_4$-$C_{10}$ aryl, furanyl, pyranyl or thiofuranyl.

3. The method according to claim 1, wherein the fluoride containing agent is tetraalkylammonium fluoride represented by Formula 4 below:

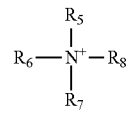
(4)

wherein $R_5$, $R_6$, $R_7$ and $R_8$ each independently represent $C_1$-$C_{20}$ alkyl or $C_6$-$C_{15}$ aryl.

4. The method according to claim 1, wherein the agent (i) and/or agent (ii) are dissolved in an aprotic polar solvent.

5. The method according to claim 1, wherein the polar aprotic solvent is at least one selected from the group consisting of DMF, DMSO, dimethylacetamide, dimethylsulfone, acetonitrile, 2-pyrrolidinone and 1-methyl-2-pyrrolidinone.

6. The method according to claim 1, wherein the phase-separation is carried out by mixing a polar solvent and a non-polar solvent with a reaction solution.

7. The method according to claim 6, wherein the polar solvent is at least one selected from the group consisting of water, ethylene glycol and acetonitrile and the non-polar solvent is at least one selected from the group consisting of xylene, benzene, toluene, methylsilene, ethylbenzene, propylbenzene, isopropylbenzene, cumene, Kokosol, petroleum ether, pentane, hexane, isohexane, heptane, octane, decane, gasoline, kerosene, light oil, ethyl ether, butylether and MTBE.

8. The method according to claim 1, wherein the step of applying the 1-alkylcyclopropene of Formula 1 to plants further comprises dissolving 1-alkylcyclopropene in a non-polar volatile solvent, followed by evaporation or dispersion.

9. The method according to claim 8, wherein the non-polar solvent is at least one selected from the group consisting of pentane, hexane, benzene, toluene, ethylbenzene, petroleum ether, ethyl ether and MTBE.

10. The method according to claim 1, wherein the step of applying the 1-alkylcyclopropene of Formula 1 to plants further comprises mixing the phase-separated 1-alkylcyclopropene with a liquid solvent, a surfactant and a stabilizing agent.

11. The method according to claim 10, wherein the liquid solvent is at least one selected from the group consisting of water, ethylene glycol, oligoethylene glycol, alcohol, pentane, hexane, benzene, toluene, ethylbenzene, petroleum ether, ethyl ether and MTBE, the surfactant is at least one selected from the group consisting of anionic surfactants and cationic surfactants, and the stabilizing agent is at least one selected from the group consisting of neutral surfactants such as water-soluble polymers or polyethylene glycols.

12. The method according to claim 1, wherein the step of applying the 1-alkylcyclopropene of Formula 1 to plants further comprises diluting the 1-alkylcyclopropene with a liquid solvent and/or a solid extender, followed by dispersion.

13. The method according to claim 12, wherein the liquid solvent is at least one selected from the group consisting of water, ethylene glycol, toluene, benzene, xylene, ethylbenzene, pentane, hexane, ethyl ether and MTBE, and the solid extender is at least one selected from the group consisting of starch, quicklime and clay.

14. The method according to claim 1, wherein the process from the preparation of 1-alkylcyclopropenes and its application to plants is completed within 50 hours.

15. A method for treating plants with alkylcyclopropene of Formula 1 according to claim 1, comprising:
mixing (i) a 1-alkylcyclopropene precursor-containing agent of Formula 2 or 3 defined in claim 1 and (ii) a fluoride containing agent, separately supplied, to prepare 1-alkylcyclopropene of Formula 1;
separating and extracting 1-alkylcyclopropene of Formula 1 from the reaction solution;
mixing the 1-alkylcyclopropene with a liquid solvent, a surfactant and a stabilizing agent;
optionally, diluting the 1-alkylcyclopropene with a liquid solvent and/or a solid extender, followed by dispersion; and
applying the extracted solution, the mixed solution of the 1-alkylcyclopropene with the liquid solvent, the surfactant and the stabilizing agent or the diluted solution to plants, wherein the steps are carried out in situ.

16. A kit for preparing 1-alkylcyclopropene in situ to treat plants with alkylcyclopropene of Formula 1 according to claim 1 in an open area, comprising:
the 1-alkylcyclopropene precursor-containing agent of Formula 2 or Formula 3 defined in claim 1;
the fluoride anion salt-containing agent defined in claim 1; and
a liquid solvent containing a polar solvent and a non-polar solvent.

17. 1-alkylcyclopropene represented by the following Formula 6, for inhibiting action of ethylene facilitating ripening and aging of plants, when applied to plants, wherein the 1-alkylcyclopropene contains an aryl group and can be thus readily analyzed, can be easily formulated and exhibits inhibitory activity on ethylene;

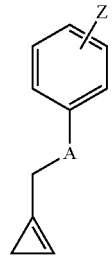

(6)

wherein A represents a straight-chain linkage having the formula of $(CH_2)_m Y(CH_2)_n$ in which m and n each independently represent an integer of 0 to 3, and Y each independently represents $CH_2$, O or S; and
Z represents at least one selected from the group consisting of hydrogen, alkyl, alkoxy, halogen, nitro and nitrile.

* * * * *